(12) United States Patent
Liu et al.

(10) Patent No.: US 9,724,041 B2
(45) Date of Patent: Aug. 8, 2017

(54) FINGERSTALL OXIMETER

(71) Applicant: Beijing Choice Electronic Technology Co., Ltd., Beijing (CN)

(72) Inventors: Shuhai Liu, Beijing (CN); Weihu Wang, Beijing (CN); Zuobin Li, Beijing (CN); Peng Wu, Beijing (CN); Wei Wang, Beijing (CN)

(73) Assignee: Beijing Choice Electronic Technology Co., Ltd., Beijing (CN)

( * ) Notice: Subject to any disclaimer, the term of this patent is extended or adjusted under 35 U.S.C. 154(b) by 393 days.

(21) Appl. No.: 14/383,298

(22) PCT Filed: Mar. 6, 2013

(86) PCT No.: PCT/CN2013/072263
§ 371 (c)(1),
(2) Date: Oct. 21, 2014

(87) PCT Pub. No.: WO2013/131482
PCT Pub. Date: Sep. 12, 2013

(65) Prior Publication Data
US 2015/0045638 A1 Feb. 12, 2015

(30) Foreign Application Priority Data
Mar. 6, 2012 (CN) .......................... 2012 1 0057401

(51) Int. Cl.
*A61B 5/1455* (2006.01)
*A61B 5/00* (2006.01)
*A61B 5/0205* (2006.01)
*A61B 5/024* (2006.01)

(52) U.S. Cl.
CPC .......... *A61B 5/6826* (2013.01); *A61B 5/0205* (2013.01); *A61B 5/14552* (2013.01); *A61B 5/02427* (2013.01); *A61B 5/6843* (2013.01)

(58) Field of Classification Search
CPC ............ A61B 5/14551; A61B 5/02416; A61B 5/14552; A61B 5/7207; A61B 5/4818; A61B 5/6826
See application file for complete search history.

(56) References Cited

U.S. PATENT DOCUMENTS

2003/0162414 A1* 8/2003 Schulz ............... A61B 5/02427
439/11
2010/0331635 A1* 12/2010 Wang ..................... A61B 5/145
600/309
2011/0054280 A1 3/2011 Yin et al.

FOREIGN PATENT DOCUMENTS

| CN | 101411618 A | 4/2009 |
| CN | WO 2009052747 A1 * | 4/2009 ......... A61B 5/14552 |
| CN | 201585988 U | 9/2010 |

(Continued)

*Primary Examiner* — Eric Winakur
(74) *Attorney, Agent, or Firm* — The Webb Law Firm (57) ABSTRACT

Disclosed is a fingerstall oximeter comprising an upper housing (11), a middle housing (12), a lower housing (13) and a detection unit. The upper housing (11), the middle housing (12) and the lower housing (13) are connected in turn. The lower housing (13) is made of silica gel, and a finger accommodating chamber (14) for accommodating a finger to be measured is formed between the opposed surfaces of the lower housing (13) and the middle housing (12). The fingerstall oximeter has high measurement accuracy and small volume, and is easy to disassemble and carry.

14 Claims, 4 Drawing Sheets

(56) References Cited

FOREIGN PATENT DOCUMENTS

| | | |
|---|---|---|
| CN | 201798745 U | 4/2011 |
| CN | 102223835 A | 10/2011 |
| CN | 201996543 U | 10/2011 |
| CN | 102525485 A | 7/2012 |
| CN | 102551737 A | 7/2012 |
| CN | 102579054 A | 7/2012 |
| CN | 202526182 U | 11/2012 |
| CN | 202553913 U | 11/2012 |
| CN | 202636952 U | 1/2013 |
| WO | 9600518 A1 | 1/1996 |
| WO | 2009140815 A1 | 11/2009 |

* cited by examiner

FINGERSTALL OXIMETER

CROSS-REFERENCE TO RELATED APPLICATIONS

This application is the United States national phase of International Application No. PCT/CN2013/072263 filed Mar. 6, 2013, and claims priority to Chinese Patent Application No. 201210057401.1 filed Mar. 6, 2012, the disclosures of which are hereby incorporated in their entirety by reference.

FIELD OF THE INVENTION

The present invention relates to a technical field of blood oxygen measurement, and particularly relates to a fingerstall oximeter.

BACKGROUND OF THE INVENTION

Oximeter is a commonly used instrument for measuring pulse and degree of blood oxygen saturation. Typical oximeter includes finger-clip oximeter, desk-top oximeter and the like, among which the finger-clip oximeter is widely used for being easy to use and carry.

Conventional finger-clip oximeter comprises an upper housing, a lower housing and a spring clip connecting the upper housing and the lower housing. A light emitting device and a light receiving device are respectively disposed in the upper housing and the lower housing, for measuring pulse and degree of blood oxygen saturation of human body. During operation, one end of the upper housing and the lower housing is pressed to make them separated for a certain angle, then a finger is placed between the upper housing and the lower housing to be clipped by the upper housing and the lower housing by means of the spring clip, such that the pulse and degree of blood oxygen saturation of human body can be measured using the light emitting device and the light receiving device. However, existing finger-clip oximeter is provided with a twist spring, the upper housing (for accommodating relevant elements including a portion contacting the finger, case locked onto this portion and the like) and the lower housing (for accommodating relevant elements including a portion contacting lower part of the finger and battery compartment for accommodating batteries) are forced by the twist spring to clip the finger, the clip force is focused on the finger tip. Therefore, the pressure at the finger tip near the twist spring is high, especially for fat fingers, such that feelings from the finger will be uncomfortable, and the blood flow would be blocked due to the high pressure on the finger, thus the blood oxygen measurement result will be affected. Moreover, when the upper housing and the lower housing are separated for a certain angle during operation, the measurement result of the finger-clip oximeter is easily interfered by ambient light, leading to lower measurement accuracy of the finger-clip oximeter.

CN patent No. 200710165004.5 disclosed a finger-type pulse and blood oxygen saturation measuring apparatus. As shown in the FIG. 1, the finger-type pulse and blood oxygen saturation measuring apparatus comprises a detection device 1, a power supply device 2 and a soft case 3. The soft case 3 comprises a socket 4 adapted to the finger shape, a first accommodating portion 5 and a second accommodating portion 6; the socket 4, the first accommodating portion 5 and the second accommodating portion 6 are integrated. The first accommodating portion 5 and the second accommodating portion 6 are disposed at the upper and lower sides of the socket 4 respectively, so as to accommodate the detection device 1 and the power supply device 2 respectively. The socket 4 is properly broadened at two sides in the lateral direction for accommodating fingers with various thicknesses, and for ensuring that the fingers of various thicknesses can be surrounded by the socket 4 to prevent the measurement result from being affected by ambient light, so as to improve measurement accuracy of the finger-type pulse and blood oxygen saturation measuring apparatus.

Figure 1:
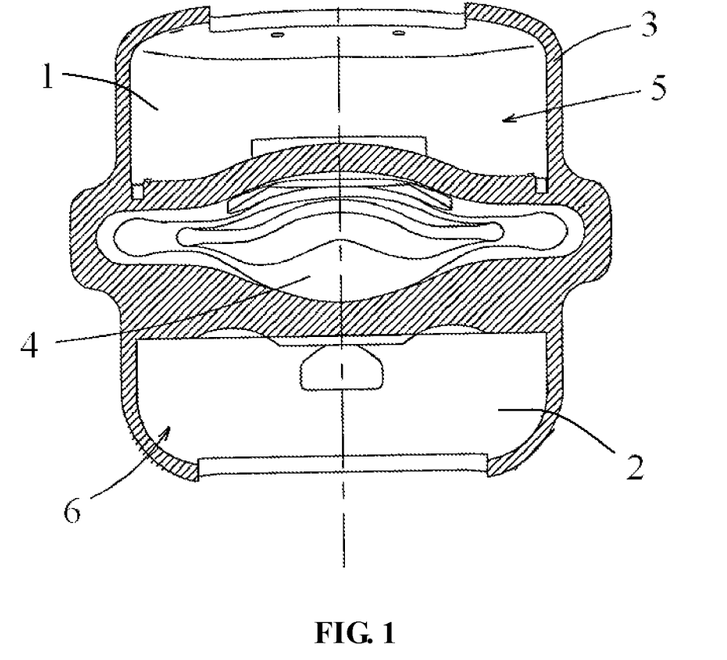
FIG. 1 is a schematic structural view of an existing finger-type pulse and blood oxygen saturation measuring apparatus.

The soft case 3 can effectively avoid the influence of the ambient light on measurement result. However, the detection device 1 and the power supply device 2 cannot be disposed within the first accommodating portion 5 and the second accommodating portion 6 without any support, but shall be provided on corresponding carriers. Thus when assembling the finger-type pulse and blood oxygen saturation measuring apparatus, firstly the detection device 1 and the power supply device 2 shall be assembled to corresponding carriers, and then be assembled with the soft case 3 together; on the other hand, when the finger-type pulse and blood oxygen saturation measuring apparatus needs maintain, the detection device 1, the power supply device 2 and the soft case 3 shall be separated firstly, then the detection device 1 and the power supply device 2 are detached from the respective carriers, leading to complicated assemble/deassemble procedure and inconvenience in assembling and maintain, and the poor firmness of the assembled apparatus. Moreover, in the structure of the finger-type pulse and blood oxygen saturation measuring apparatus, since the detection device 1 and the power supply device 2 are disposed separately in the first/second accommodating portions, the thickness of the apparatus (i.e. the perpendicular distance from the upper surface of the first accommodating portion 5 to the lower surface of the second accommodating portion 6) is large and is not easy to carry.

SUMMARY OF THE INVENTION

To solve one of the above problems, the present invention provides a fingerstall oximeter which can effectively reduce the influence of ambient light to the measurement result, has a small volume and is easy to be assembled/disassembled.

A solution to solve the above technical problem is a fingerstall oximeter comprising: an upper housing, a middle housing, a lower housing and a detection unit, wherein the upper housing, the middle housing and the lower housing are connected in turn, the lower housing is made of silica gel, and a finger accommodating chamber for accommodating a finger under detection is formed between the opposed surfaces of the lower housing and the middle housing.

Preferably, the lower housing is connected with the middle housing by means of adhesive or connector.

Preferably, the peripheries of the opposed surfaces of the upper housing and the middle housing are respectively the pressure junction surfaces of the upper housing and the middle housing, and the edge of the lower housing is pressed between the pressure junction surfaces of the upper housing and the middle housing such that the lower housing connects with the middle housing.

Preferably, the lower housing comprises an arc portion and a connection portion, the arc portion projects towards a direction away from the middle housing, and the connection portion is pressed between the pressure junction surfaces of the upper housing and the middle housing.

Preferably, the lower housing further comprises an extension portion located between the connection portion and the arc portion, the internal contour of the extension portion has the same shape as the external contour of the corresponding part in the middle housing.

Preferably, a first positioning hole is provided in the connection portion, a first positioning post is provided on the pressure junction surface of the middle housing at a position corresponding to the first positioning hole. The first positioning hole matches the first positioning post, by means of which the middle housing and the lower housing are positioned accurately.

Preferably, the middle housing comprises a first portion and a second portion, wherein the first portion has a lateral external diameter equal to that of the lower housing, the second portion has a lateral external diameter less than that of the first portion, and the longitudinal length of the second portion is substantially equal to that of the lower housing. The extension portion of the lower housing covers the outer surface of the second portion of the middle housing, and the connection portion of the lower housing seals the gap between the pressure junction surface of the second portion of the middle housing and the pressure junction surface of the upper housing at a corresponding position.

Preferably, the fingerstall oximeter further comprises a sealing plate, which is provided between the pressure junction surface of the first portion of the middle housing and the pressure junction surface of the upper housing, and seals the gap between the pressure junction surface of the first portion of the middle housing and the pressure junction surface of the upper housing at a corresponding position.

Preferably, a second positioning hole is provided in the sealing plate, a second positioning post is provided on the pressure junction surface of the middle housing at a position corresponding to the second positioning hole, and the second positioning hole matches the second positioning post.

Preferably, the sealing plate is connected with the connection portion, and the sealing plate and the lower housing are formed as a whole.

Preferably, a concave portion recessed towards the direction of the upper housing is provided at a position of the middle housing opposite to the arc portion of the lower housing, and the concave portion is disposed along the longitudinal direction of the middle housing.

Preferably, a positioning portion is provided at the back end of the finger accommodating chamber to position the finger inserting into the chamber.

The present invention has the following advantages.

The fingerstall oximeter according to the present invention utilizes a split type structure in which an upper housing, a middle housing and a lower housing are connected in turn; when assembled, firstly the internal components are disposed within corresponding housings and then the housings are in turn amounted to finish assembly, such that the fingerstall oximeter can be easily assembled/disassembled. A finger accommodating chamber for accommodating the finger is formed between the lower housing and the middle housing, the lower housing is made of silica gel, when the finger inserts into the finger accommodating chamber formed by the lower housing and the middle housing, the finger is surrounded by the lower housing made of silica gel, so as to prevent side light from entering the finger accommodating chamber. Furthermore, the finger under detection is applied with uniform pressure by means of surrounding of the silica gel, which maintains a normal blood flow in the finger under detection, further ensures accuracy of the measurement and avoids the problems resulted from the spring clip. Therefore, the fingerstall oximeter according to the present invention has high measurement accuracy and is easy to be assembled/disassembled, thus the efficiency of industrial production and assembly can be improved.

DETAILED DESCRIPTION OF THE PREFERRED EMBODIMENTS

In order to make persons skilled in the art better understand the technical solutions of the present invention, the fingerstall oximeter provided by the present invention will be described in detail below in combination with the figures.

Figure 2:
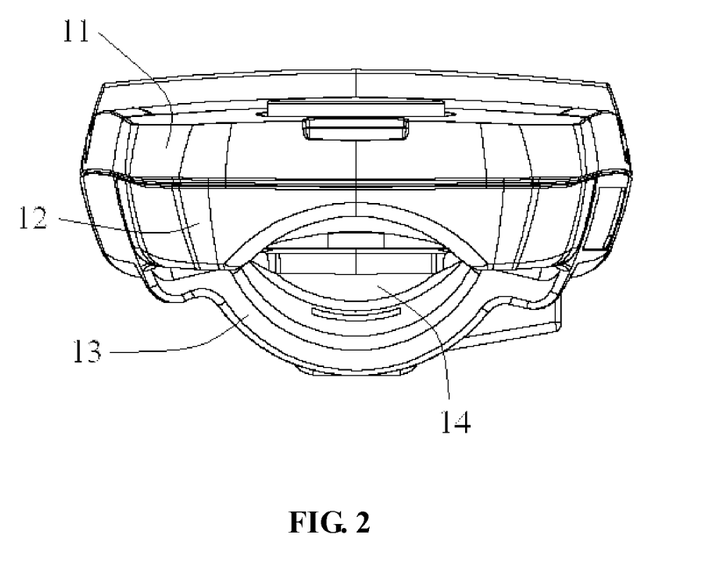
FIG. 2 is a schematic structural view of the fingerstall oximeter according to an embodiment of the present invention.
Figure 3:
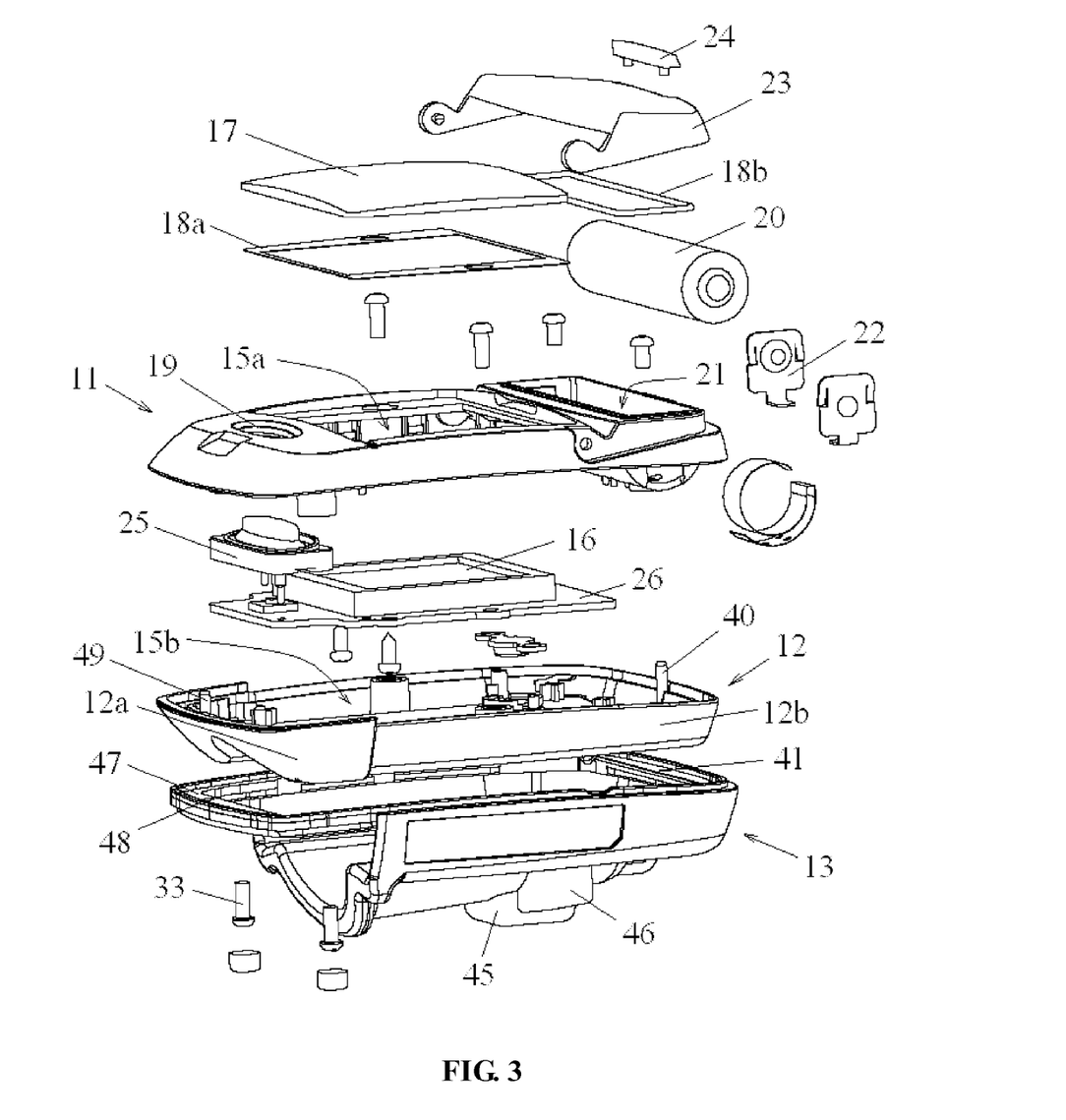
FIG. 3 is an exploded view of the fingerstall oximeter according to an embodiment of the present invention.

FIG. 2 is a schematic structural view of the fingerstall oximeter according to an embodiment of the present invention, and FIG. 3 is an exploded view of the fingerstall oximeter according to an embodiment of the present invention. Referring to FIGS. 2 and 3, the fingerstall oximeter comprises housings, a finger accommodating chamber 14 and a detection unit disposed in the housings, wherein the housings comprises an upper housing 11, a middle housing 12 and a lower housing 13, and the upper housing 11, the middle housing 12 and the lower housing 13 are connected in turn from top to bottom. A finger accommodating chamber 14 is formed between the opposed surfaces of the lower housing 13 and the middle housing 12, that is, the lower surface of the middle housing 12 and the upper surface of the lower housing 13 surrounds to form the finger accommodating chamber 14.

The detection unit comprises a luminous tube (not shown in the figures), a light detector 27, a data processing unit, a battery 20 and a display screen 16, wherein the battery 20 and the display screen 16 are disposed in the upper housing 11, the light detector 27 and the data processing unit are disposed in the middle housing 12, the light detector 27 is connected with the data processing unit, and the luminous tube is disposed in the lower housing 13.

For convenience of description, in the embodiment, the front end (front side) of the fingerstall oximeter refers to the end of the insertion opening of the finger accommodating chamber 14, the opposite end is the back end (back side) of the fingerstall oximeter. When viewed from the front end to the back end, the left side of the fingerstall oximeter is located at the left hand side, and the right side of the fingerstall oximeter is located at the right hand side. The line from the front end to the back end of the fingerstall oximeter is the longitudinal direction of the fingerstall oximeter, and the line from the left side to the right side of the fingerstall oximeter is the lateral direction of the fingerstall oximeter.

The upper housing 11 is located above the fingerstall oximeter, and the lower housing 13 is located below the fingerstall oximeter.

Figure 4:
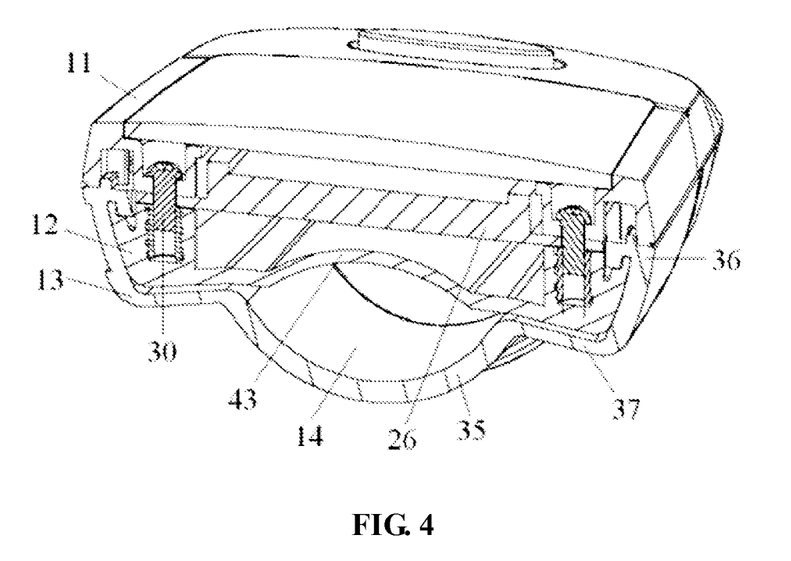
FIG. 4 is a lateral sectional view of the fingerstall oximeter according to an embodiment of the present invention.
Figure 5:
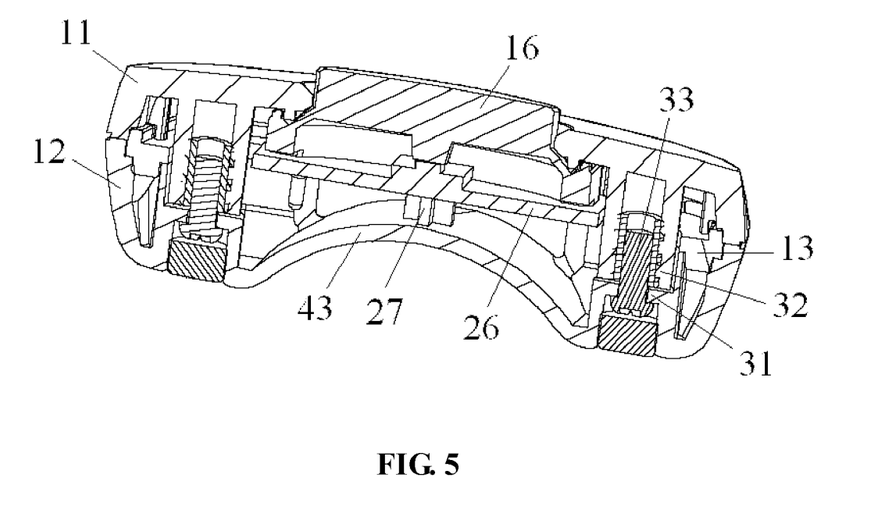
FIG. 5 is a lateral sectional view of a part of the fingerstall oximeter according to an embodiment of the present invention.

FIG. 4 is a lateral sectional view of the fingerstall oximeter according to an embodiment of the present invention, and FIG. 5 is a lateral sectional view of a part of the fingerstall oximeter according to an embodiment of the present invention; wherein FIG. 5 is a cross-section through the light detector, and FIG. 4 is a cross-section between the light detector and the battery compartment. Referring to FIGS. 3 to 5, the upper housing 11 and the middle housing 12 are connected by a fastening piece, and the lower housing 13 and the middle housing 12 are connected by adhesive or a connector. Of course, the lower housing 13 can be pressed between the upper housing 11 and the middle housing 12.

Specifically, as shown in FIG. 4, the lower housing 13 comprises an arc portion 35 and a connection portion 36, and the arc portion 35 projects towards a direction away from the middle housing 12, i.e. the arc portion 35 projects towards the bottom of the fingerstall oximeter. The connection portion 36 is provided at the left side, the right side and the back side of the arc portion 35, that is, the connection portion 36 is provided at all the sides except the side of the insertion opening of the finger accommodating chamber 14; the connection portion 36 connects the lower housing 13 with the middle housing 12, and is pressed between the pressure junction surfaces of the upper housing 11 and the middle housing 12.

Preferably, the lower housing 13 further comprises an extension portion 37 located between the connection portion 36 and the arc portion 35, the internal contour of the extension portion 37 has the same shape as the external contour of the corresponding part in the middle housing 12, such that the fingerstall oximeter has a compact structure and a reduced volume, and is easy to carry.

Note that in the present embodiment, the lower housing 13 may not be provided with the arc portion 35, that is, the lower housing 13 may be a planar plate structure without an arc portion. However in practice, the arc portion 35 is advantageous for inserting a finger into the finger accommodating chamber 14.

Referring to FIG. 3, a first positioning hole 41 is provided in the connection portion 36, and a first positioning post 40 is provided on the pressure junction surface of the middle housing 12 at a position corresponding to the first positioning hole 41. The first positioning hole 41 matches the first positioning post 40, by means of which the middle housing 12 and the lower housing 13 are positioned accurately, such that assembly of the fingerstall oximeter is facilitated. Note that the number of the first positioning hole 41 and the first positioning post 40 is not limited to two, but may be three or more, provided that the number of the first positioning hole 41 is equal to the number of the first positioning post 40.

In the present embodiment, the lower housing 13 is made of silica gel. Since silica gel has good elasticity, the gap between the pressure junction surfaces of the upper housing 11 and the middle housing 12 can be sealed well, preventing liquid or dust from entering inside of the fingerstall oximeter through the pressure junction surfaces of the upper housing 11 and the middle housing 12. Moreover, when a finger inserts into the fingerstall oximeter, the finger under detection would be hold by shrinkage force of the silica gel and is not easily pulled-off, the lower housing 13 made of silica gel can increase or reduce the volume of the finger accommodating chamber 14, such that the application range of the fingerstall oximeter is enlarged. Compared to the conventional finger-clip oximeter, the fingerstall oximeter according to the present invention can be adapted to fingers with various thicknesses and applies uniform pressure to the finger, such that accuracy of measurement result can be ensured, and the spring-clip associated problem resulted from the twist spring and the like in the finger-clip oximeter can be avoided. Furthermore, the performance of fall-assist and shock-assist of the fingerstall oximeter can be improved. In the embodiment, a large part of the surface of the middle housing 12 is surrounded by the extension portion 37 of the lower housing 13, which reduces the possibility of the middle housing 12 contacting external objects, increases lifetime of the fingerstall oximeter, and improves the touch feeling of the fingerstall oximeter. The shrinkage force of silica gel can make the lower housing 13 contact the finger closely, such that the ambient light entering into the finger accommodating chamber 14 can be reduced and the accuracy of measurement result can be improved.

In the present embodiment, in order to provide a fingerstall oximeter with a compact structure, the middle housing 12 is divided into a first portion 12a and a second portion 12b in the longitudinal direction, wherein the first portion 12a has a lateral external diameter equal to that of the lower housing 13, the second portion 12b has a lateral external diameter less than that of the first portion 12a, and the longitudinal length of the second portion 12b is substantially equal to that of the lower housing 13. The extension portion 37 of the lower housing 13 surrounds the outer surface of the second portion 12b of the middle housing 12.

In the present embodiment, since the longitudinal length of the lower housing 13 is less than that of the middle housing 12, the connection portion 36 of the lower housing 13 can only seal part of the gap between the pressure junction surface of the upper housing 11 and the pressure junction surface of the middle housing 12, that is, can only seal the gap between the pressure junction surface of the second portion 12b of the middle housing 12 and the pressure junction surface of the upper housing 11 at a corresponding position, but the pressure junction surface corresponding to the first portion 12a of the middle housing 12 is not sealed.

For this, a "U" shape sealing plate 47 made of elastic material is provided between the pressure junction surface of the first portion 12a of the middle housing 12 and the pressure junction surface of the upper housing 11, and the sealing plate 47 seals the gap between the pressure junction surface of the first portion 12a of the middle housing 12 and the pressure junction surface of the upper housing 11 at a corresponding position.

Besides, in the present embodiment, a second positioning hole 48 is provided in the sealing plate 47, and a second positioning post 49 is provided on the pressure junction surface of the middle housing 12 at a position corresponding to the second positioning hole 48, and the second positioning hole 48 matches the second positioning post 49. During assembly of the sealing plate 47, the sealing plate 47 can be accurately connected with the middle housing 12 by means of the second positioning hole 48 and the second positioning post 49, such that the sealing plate 47 can be placed accurately at corresponding positions on the pressure junction surfaces of the upper housing 11 and the middle housing 12. It can be understood that a plurality of second positioning holes 48 and second positioning posts 49 can be provided correspondingly on the pressure junction surfaces of the sealing plate 47 and the middle housing 12.

Preferably, the sealing plate 47 and the lower housing 13 are formed as a whole, the sealing plate 47 is located in a plane coplanar with the upper surface of the connection portion 36, an enclosed ring is formed by the sealing plate 47 and top of the connection portion 36 of the lower housing 13 together and covers the entire pressure junction surfaces of the upper housing 11 and the middle housing 12.

Referring to FIG. 3, in the present embodiment, a first accommodating space 15a is set in the middle of the upper housing 11 for accommodating the display screen 16. A measurement apparatus end cap 17 is provided above the display screen 16 for protecting the display screen 16. A first sealing plate 18a is disposed between the pressure junction surfaces of the display screen 16 and the upper housing 11, and the first sealing plate 18a can effectively prevent dust and water from entering the upper housing 11, such that the water-proof performance of the fingerstall oximeter is improved.

A battery compartment 21 for accommodating the battery 20 is provided at a position close to the back end of the upper housing 11, and the battery compartment 21 is disposed along the lateral direction of the upper housing 11, thus a display screen 16 with a larger size can be provided for displaying enlarged contents. Electric connectors 22 are disposed respectively at the left and right sides inside the battery compartment 21. A battery compartment cap 23 is disposed above the battery compartment 21 for covering the opening of the battery compartment 21. A second sealing plate 18b is disposed between the pressure junction surfaces of the battery compartment cap 23 and the battery compartment 21 to seal the gap between the pressure junction surfaces of the battery compartment cap 23 and the upper housing 11, preventing dust and water from entering the battery compartment 21, such that the water-proof performance of the fingerstall oximeter is improved. An opening button 24 for the battery compartment cap is provided on top of the battery compartment cap 23 for opening the battery compartment cap 23.

A second accommodating space 15b is set within the middle housing 12, and the data processing circuit 26 and the light detector 27 are disposed in the second accommodating space 15b. The data processing circuit 26 is fixed into the middle housing 12 through screw 30. The data processing circuit 26 is connected with the display screen 16, the battery 20 and the light detector 27. The data processing circuit 26 receives and processes signals from the light detector 27, obtains pulse and degree of blood oxygen saturation, and then outputs the pulse and degree of blood oxygen saturation to the display screen 16 so that a user can visually read out the pulse and degree of blood oxygen saturation.

In the present embodiment, after the upper housing 11 is completely locked onto the middle housing 12, the first accommodating space 15a of the upper housing 11 communicates with the second accommodating space 15b of the middle housing 12, so as to form a single space. The battery compartment 21 is disposed at the back end of the upper housing 11 and projects towards the middle housing. After the upper housing 11 is completely locked onto the middle housing 12, the projection portion of the battery compartment 21 is embedded into the second accommodating space 15b of the middle housing 12, such that the battery compartment 21 is located in a space enclosed by the upper housing 11 and the middle housing 12. Compared to the prior art in which the detection device 1 and the power supply device 2 are disposed at two sides of the finger-shaped socket 4 respectively, the thickness of the measurement apparatus is effectively reduced, the fingerstall oximeter has a smaller volume and is easy to carry. Note that in the present embodiment, the light detector 27 is disposed in the middle housing 12 and the luminous tube is disposed in the lower housing 13. However in practice, the positions of the light detector 27 and the luminous tube can be exchanged, i.e. the light detector 27 is disposed in the lower housing 13 and the luminous tube is disposed in the middle housing 12, the pulse and degree of blood oxygen saturation can be also obtained accurately.

A power supply button 25 for turning on/off the fingerstall oximeter is connected with the data processing circuit 26. The power supply button 25 protrudes from a button through hole 19 provided on the front end of the upper housing 11, such that the fingerstall oximeter can be easily powered on/off.

Since different components are disposed in the upper housing 11, the middle housing 12 and the lower housing 13 respectively, when the fingerstall oximeter is assembled, firstly the components are fixed to corresponding positions, then the middle housing 12, the lower housing 13 and the upper housing 11 are in turn amounted to finish the assembly; while in the prior art, all the housings need to be fixed and plugged in a certain order, so as to finish the assembly. Therefore the fingerstall oximeter according to the embodiment of the present invention is easier to be assembled.

Furthermore, in the present embodiment, except the luminous tube or the light detector 27, all the other components are disposed above the finger accommodating chamber 14 (i.e. the chamber formed by the upper housing 11 and the middle housing 12). These main components are where fault most likely occurs. Thus, in most situations, users only need to detach the upper housing from other housings and perform maintenance.

Referring to FIG. 4, in order to facilitate a finger inserting into the finger accommodating chamber 14, a concave portion 43 recessed towards the direction of the upper housing 12 is provided at the opening of the finger accommodating chamber 14 at the front end of the middle housing 12. The concave portion 43 and the arc portion 35 of the lower housing 13 enlarges the opening of the finger accommodating chamber 14, such that a finger can be inserted into the finger accommodating chamber 14 easily.

A positioning portion (not shown in the figures) is provided at the back end of the finger accommodating chamber 14, and the positioning portion is used for positioning the finger inserting into the finger accommodating chamber 14. When the finger tip of a user touches the positioning portion, it is determined that the finger is at a desired position for measuring blood oxygen. It can be understood that the positioning portion simplifies the measuring procedure of the fingerstall oximeter.

Referring to FIG. 5, the upper housing 11 and the middle housing 12 are connected by fastening screw 33. Of course, other fastening piece such as screw bolt and the like can be used. In particular, a first connection hole 31 throughout the thickness of the middle housing 12 is provided in the middle housing 12, a first connection post 32 is provided on the lower surface of the upper housing 11 at a position opposed to the first connection hole 31. Thread is provided inside the first connection hole 31 for matching the fastening screw 33, the fastening screw 33 passes through the first connection hole 31 and matches the thread so as to connect the upper housing 11 with the middle housing 12. The upper housing 11 and the middle housing 12 are both made of hard material, so when they are assembled or disassembled, the assembly/disassembly can be completed only by fastening or loosening the fastening screw 33; such a solution is easier than the prior art solution in which the soft case 3 surrounds the entire measurement apparatus.

When the fingerstall oximeter is assembled, the outer surface of the middle housing 12 is covered by the extension portion 37 of the lower housing 13, the connection portion 36 of the lower housing 13 and the sealing plate 47 are closely locked onto the pressure junction surface of the middle housing 12, and then the upper housing 11 is locked onto the middle housing 12 such that the edge of the upper housing 11 tightly touch the connection portion 36 of the lower housing 13 and the sealing plate 47, the upper housing 11 is then connected with the middle housing 12 through a fastening piece such as fixing screw bolt, and finally the measurement apparatus end cap 17 is adhered to the upper housing 11.

Figure 6:
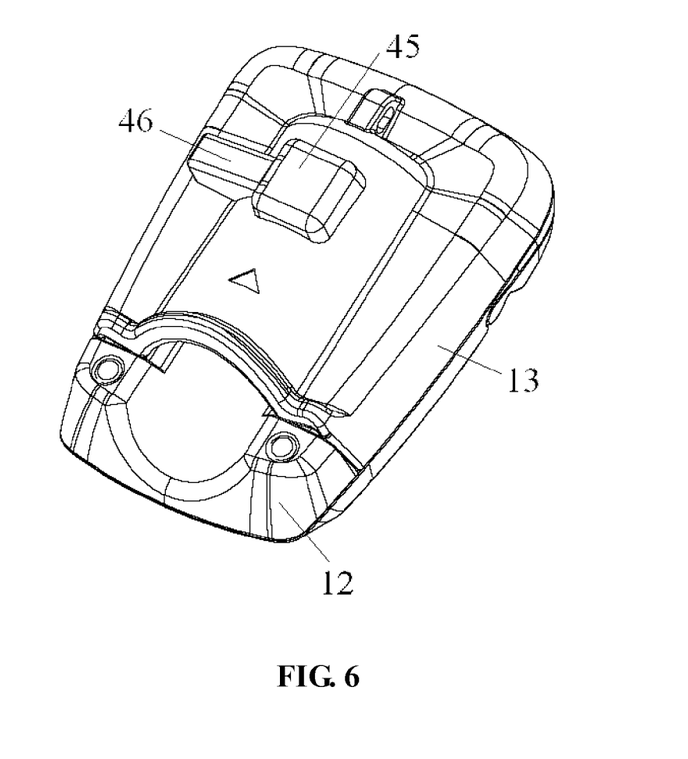
FIG. 6 is a bottom view of the fingerstall oximeter according to an embodiment of the present invention.
Figure 7:
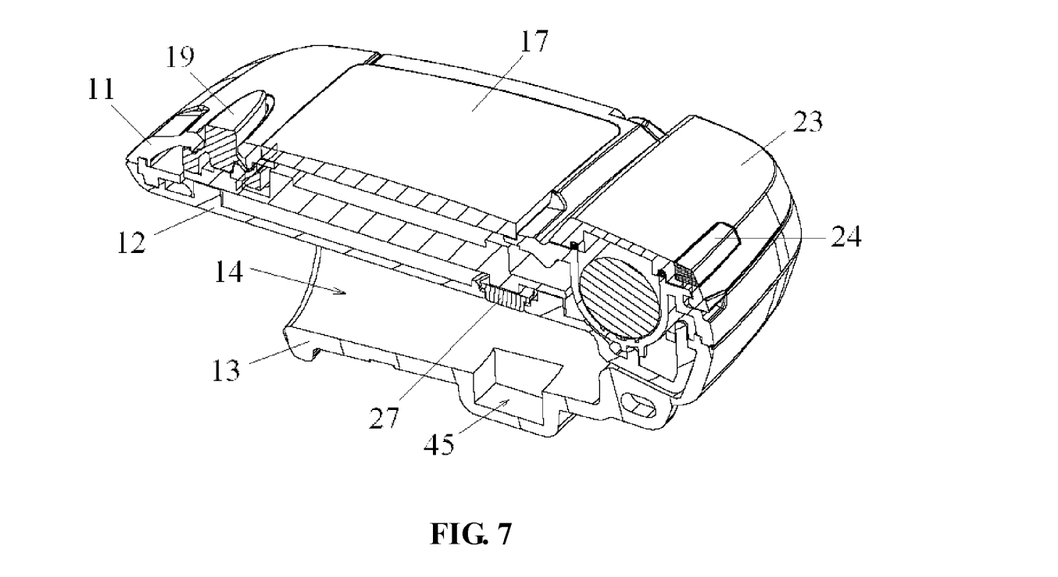
FIG. 7 is a longitudinal sectional view of the fingerstall oximeter according to an embodiment of the present invention.

FIG. 6 is a bottom view of the fingerstall oximeter according to an embodiment of the present invention, and FIG. 7 is a longitudinal sectional view of the fingerstall oximeter according to an embodiment of the present invention. Referring to FIGS. 6 and 7, a luminous tube channel 45 and a wiring channel 46 are provided at the bottom of the lower housing 13, the luminous tube channel 45 and the wiring channel 46 project towards a direction away from the middle housing 12 (i.e. towards the lower part of the fingerstall oximeter), the luminous tube is disposed in the luminous tube channel 45, and a conducting wire for connecting the luminous tube and the data processing circuit 26 is disposed in the wiring channel 46. After the luminous tube is disposed in the luminous tube channel 45, and top of the luminous tube channel 45 is sealed using transparent silica gel. The transparent silica gel can prevent water and dust from entering the luminous tube channel 45, and does not affect brightness of the light emitted from the luminous tube.

The fingerstall oximeter according to the embodiment of the present invention utilizes a split type structure in which an upper housing, a middle housing and a lower housing are in turn connected, such that the fingerstall oximeter can be easily assembled/disassembled. A finger accommodating chamber for accommodating the finger is formed between the lower housing and the middle housing, and the lower housing is made of silica gel. The lower housing can reduce the gap between the finger and the finger accommodating chamber, such that the ambient light can be prevented from entering the finger accommodating chamber, and then the accuracy of the measurement result can be improved. Therefore, the fingerstall oximeter according to the present invention has high measurement accuracy and is easy to be assembled/disassembled.

It should be understood that the embodiments mentioned above are exemplary embodiments used to describe the inventive principle. However, the present invention is not limited thereto. It is obvious to those skilled in the art, various modifications and improvements can be made without departing from the spirit and substance of the present invention, and all the modifications and improvements are considered to be within the scope of the invention.

The invention claimed is:

1. A fingerstall oximeter, comprising: an upper housing, a middle housing, a lower housing and a detection unit, wherein the upper housing, the middle housing and the lower housing are connected in turn, the lower housing is made of silica gel, and a finger accommodating chamber for accommodating a finger under detection is formed between the opposed surfaces of the lower housing and the middle housing; wherein the lower housing comprises an arc portion, a connection portion and an extension portion located between the connection portion and the arc portion, the extension portion of the lower housing covers the outer surface of a part of the middle housing, and the internal contour of the extension portion has the same shape as the external contour of the corresponding part in the middle housing.

2. The fingerstall oximeter of claim 1, wherein the lower housing is connected with the middle housing by means of adhesive or connector.

3. The fingerstall oximeter of claim 1, wherein the peripheries of the opposed surfaces of the upper housing and the lower housing are the pressure junction surfaces of the upper housing, the peripheries of the opposed surfaces of the middle housing and the upper housing are the pressure junction surfaces of the middle housing, and the edge of the lower housing is pressed between the pressure junction surfaces of the upper housing and the middle housing such that the lower housing connects with the middle housing.

4. The fingerstall oximeter of claim 3, wherein the arc portion projects towards a direction away from the middle housing, and the connection portion is pressed between the pressure junction surfaces of the upper housing and the middle housing.

5. The fingerstall oximeter of claim 4, wherein a first positioning hole is provided in the connection portion, a first positioning post is provided on the pressure junction surface of the middle housing at a position corresponding to the first positioning hole, and the first positioning hole matches the first positioning post, and the middle housing and the lower housing are positioned accurately by means of the first positioning hole and the first positioning post.

6. The fingerstall oximeter of claim 4, wherein the middle housing comprises a first portion and a second portion, wherein the first portion has a lateral external diameter equal to that of the lower housing, the second portion has a lateral external diameter less than that of the first portion, and the longitudinal length of the second portion is substantially equal to that of the lower housing, the extension portion of the lower housing covers the outer surface of the second portion of the middle housing, and the connection portion of the lower housing seals the gap between the pressure junction surface of the second portion of the middle housing and the pressure junction surface of the upper housing at a corresponding position.

7. The fingerstall oximeter of claim 6, further comprising a sealing plate which is provided between the pressure junction surface of the first portion of the middle housing and the pressure junction surface of the upper housing, and seals the gap between the pressure junction surface of the first portion of the middle housing and the pressure junction surface of the upper housing at a corresponding position.

8. The fingerstall oximeter of claim 7, wherein a second positioning hole is provided in the sealing plate, a second positioning post is provided on the pressure junction surface of the middle housing at a position corresponding to the second positioning hole, and the second positioning hole matches the second positioning post.

9. The fingerstall oximeter of claim 7, wherein the sealing plate is connected with the connection portion, and the sealing plate and the lower housing are formed as a whole.

10. The fingerstall oximeter of claim 4, wherein a concave portion recessed towards the direction of the upper housing is provided at a position of the middle housing opposite to the arc portion of the lower housing, and the concave portion is disposed along the longitudinal direction of the middle housing.

11. The fingerstall oximeter of claim 1, wherein a positioning portion is provided at the back end of the finger accommodating chamber to position the finger inserting into the chamber.

12. The fingerstall oximeter of claim 1, wherein the upper housing and the middle housing are connected by a screw, a first connection hole throughout the thickness of the middle housing is provided in the middle housing, a first connection post is provided on the lower surface of the upper housing at a position opposed to the first connection hole, thread is provided inside the first connection hole for matching the screw, the screw passes through the first connection hole and matches the thread so as to connect the upper housing with the middle housing.

13. The fingerstall oximeter of claim 1, wherein a light detector and a data processing circuit for measuring pulse and degree of blood oxygen saturation are disposed in the middle housing, a luminous tube is disposed in the lower housing, a luminous tube channel and a wiring channel are provided at the bottom of the arc portion, the luminous tube channel and the wiring channel project towards a direction away from the middle housing, the luminous tube is disposed in the luminous tube channel, and a conducting wire for connecting the luminous tube and the data processing circuit is disposed in the wiring channel.

14. The fingerstall oximeter of claim 1, wherein a battery compartment for accommodating a battery is provided at the back end of the upper housing, and the battery compartment is disposed in the upper housing along the lateral direction of the upper housing.

* * * * *